US012295563B2

(12) United States Patent
Solitro et al.

(10) Patent No.: US 12,295,563 B2
(45) Date of Patent: May 13, 2025

(54) BUTTON FOR ANCHORING OF MULTIPLE SUTURES

(71) Applicant: Board of Supervisors of Louisiana State University and Agricultural and Mechanical College, Baton Rouge, LA (US)

(72) Inventors: Giovanni Francesco Solitro, Shreveport, LA (US); Patrick Massey, Shreveport, LA (US)

( * ) Notice: Subject to any disclaimer, the term of this patent is extended or adjusted under 35 U.S.C. 154(b) by 0 days.

(21) Appl. No.: 17/067,630

(22) Filed: Oct. 9, 2020

(65) Prior Publication Data

US 2021/0106321 A1 Apr. 15, 2021

Related U.S. Application Data

(60) Provisional application No. 62/913,130, filed on Oct. 9, 2019.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0404* (2013.01); *A61B 2017/0414* (2013.01); *A61F 2002/0852* (2013.01); *A61F 2002/0882* (2013.01)

(58) Field of Classification Search
CPC ........ A61B 17/0401; A61B 2017/0404; A61B 2017/0414; A61F 2/0811; A61F 2002/0882; A61F 2002/0852
See application file for complete search history.

(56) References Cited

U.S. PATENT DOCUMENTS

| | | | | |
|---|---|---|---|---|
| 5,693,060 | A * | 12/1997 | Martin | A61B 17/12013 606/148 |
| 8,029,535 | B2 * | 10/2011 | Ortiz | A61F 5/0086 606/232 |
| 8,864,797 | B2 * | 10/2014 | Justin | A61B 17/0487 606/232 |
| 9,265,498 | B2 * | 2/2016 | Fallin | A61B 17/0487 |
| 9,757,113 | B2 * | 9/2017 | Pasquali | A61F 2/0811 |
| 10,426,595 | B2 * | 10/2019 | Senior | A61F 2/0811 |
| 11,071,537 | B2 * | 7/2021 | Orphanos | A61B 17/0401 |

* cited by examiner

*Primary Examiner* — Phong Son H Dang
(74) *Attorney, Agent, or Firm* — Jones Walker LLP

(57) ABSTRACT

A suture anchor comprising a footing with a base defining a first, a second, a third, and a fourth base suture passage, a first and a second primary suture passage aligned with a primary level and fluidly connected to the first and second base suture passage for a first suture, a suture channel aligned with a secondary level spaced further from the base than the primary level, and fluidly connected to the third and fourth base suture passages a second suture, and a suture course for the first suture along a tertiary level defined by a top that is spaced further from the base than the secondary level.

20 Claims, 19 Drawing Sheets

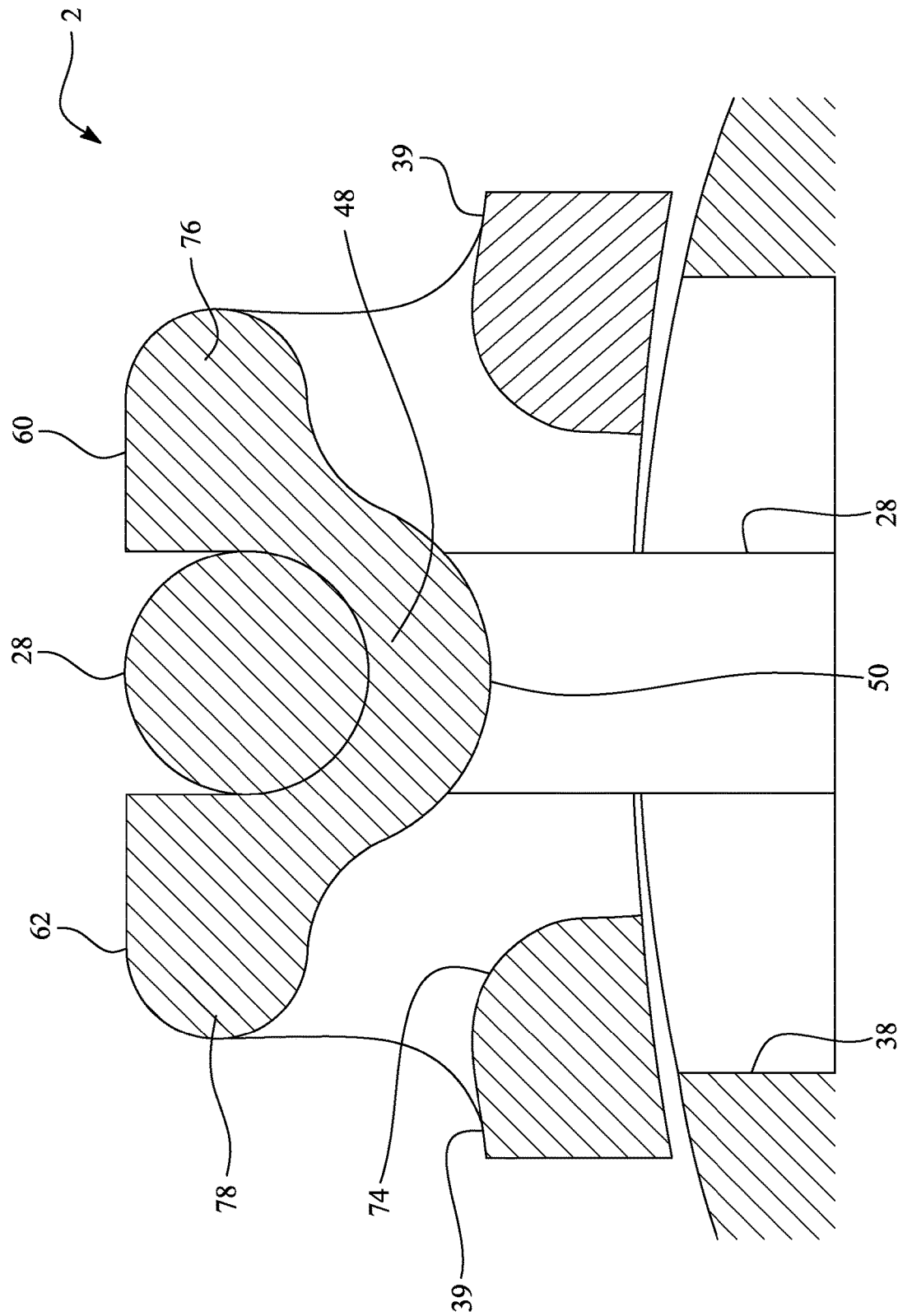

BUTTON FOR ANCHORING OF MULTIPLE SUTURES

CROSS REFERENCE TO RELATED APPLICATIONS/PRIORITY

The present invention claims priority to U.S. Provisional Patent Application No. 62/913,130 filed Oct. 9, 2019, which is incorporated by reference into the present disclosure as if fully restated herein. Any conflict between the incorporated material and the specific teachings of this disclosure shall be resolved in favor of the latter. Likewise, any conflict between an art-understood definition of a word or phrase and a definition of the word or phrase as specifically taught in this disclosure shall be resolved in favor of the latter.

BACKGROUND

During orthopedic surgery, it is sometimes necessary to tie sutures around a post to secure the sutures. Some options which can be used are a simple screw or a metal or plastic button with two holes in it, through which the sutures are passed. When using an adjustable suture strand loop in addition to a wider suture tape, there may be a significant amount of friction between the two sutures, making it difficult for the suture to slide, compromising the efficacy of the operation. Also, when passing two sets of suture or tape through one hole and tying over separate holes in a button, the sutures are tented at the hole location, causing excess friction and wear on the sutures. Many popular devices in this field are well described in the U.S. Pat. No. 9,179,950 B2 and U.S. Pat. No. 9,421,007 B2.

SUMMARY

Wherefore, it is an object of the present invention to overcome the above-mentioned shortcomings and drawbacks associated with the current technology.

The presently disclosed invention is a new type of suture fixation device where multiple sets of sutures or tape can be fixated on a metal or synthetic device, but each set of sutures will be substantially not in contact with the other suture or tape sets. However, this device also maintains the sutures close together at the drill tunnel site.

The new fixation device can be used to fix two bones with a ligament connecting the two bones. The following are examples: to fix the coracoid and clavicle, to fix the tibia and fibula at the ankle. Different size buttons can be used for different joints. Existing devices for similar repair do not guarantee absence of interference between cross sutures.

The present invention is directed to methods and suture anchors comprising a footing with a base defining a first, a second, a third, and a fourth base suture passage, a first and a second primary suture passage aligned with a primary level and fluidly connected to the first and second base suture passage for a first suture, a suture channel aligned with a secondary level spaced further from the base than the primary level, and fluidly connected to the third and fourth base suture passages a second suture, and a suture course for the first suture along a tertiary level defined by a top that is spaced further from the base than the secondary level.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIG. 7 is a cross sectional view of the suture anchor and suture strand of FIG. 8B, along the sectional line F7, mounted on a bone over a bone tunnel;

DETAILED DESCRIPTION

Figure 1:
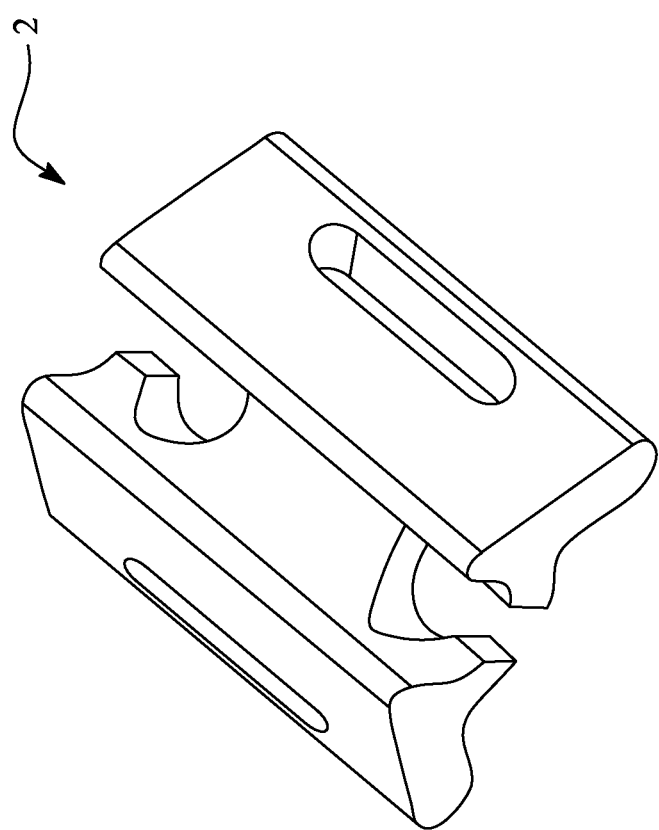
FIG. 1 is a drawing of an embodiment of the suture anchor disclosed herein.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-18C, a brief description concerning the various components of the present invention will now be briefly discussed. As can be seen in these embodiments the suture anchor 2 comprises a body 4 with a base 6, with a first, a second, a third, and a fourth base suture passage 8, 10, 12, 14 defined therein, a first and a second primary suture passage 16, 18 aligned with a primary level 20 for a first suture 22, a suture channel 24 aligned with the secondary level 26 and fluidly connected to the third and fourth base suture passages 12, 14 for a second suture 28, and a suture course 30 along a tertiary level 32 defined by a top 34. The various aspects of the suture anchor 2 and its uses will be discussed in further detail below.

Figure 2:
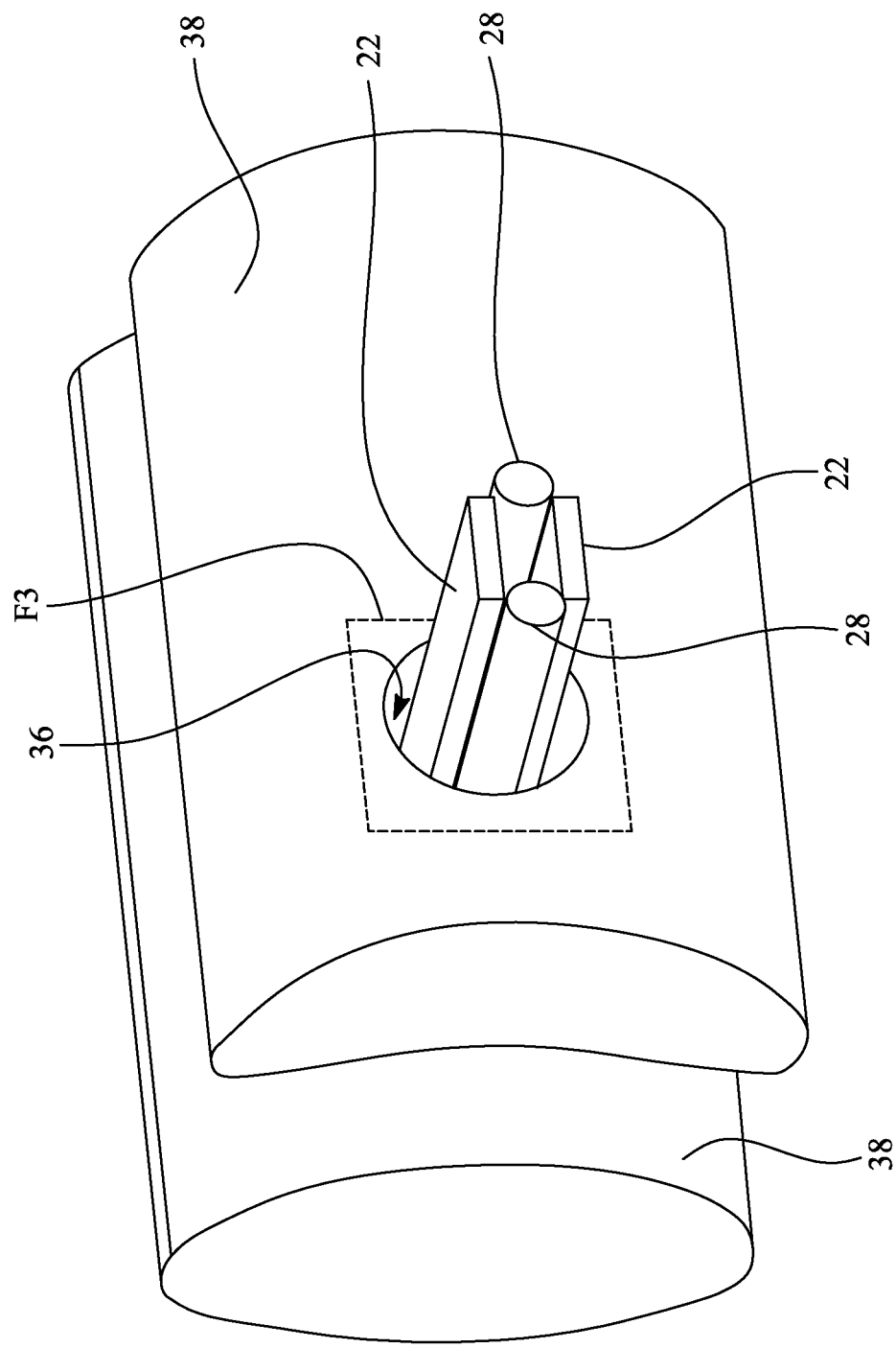
FIG. 2 is a perspective view of a simplified model of two bones hosting two independent sutures, two lines of a single suture strand, and two lines of a single suture tape.
Figure 3:
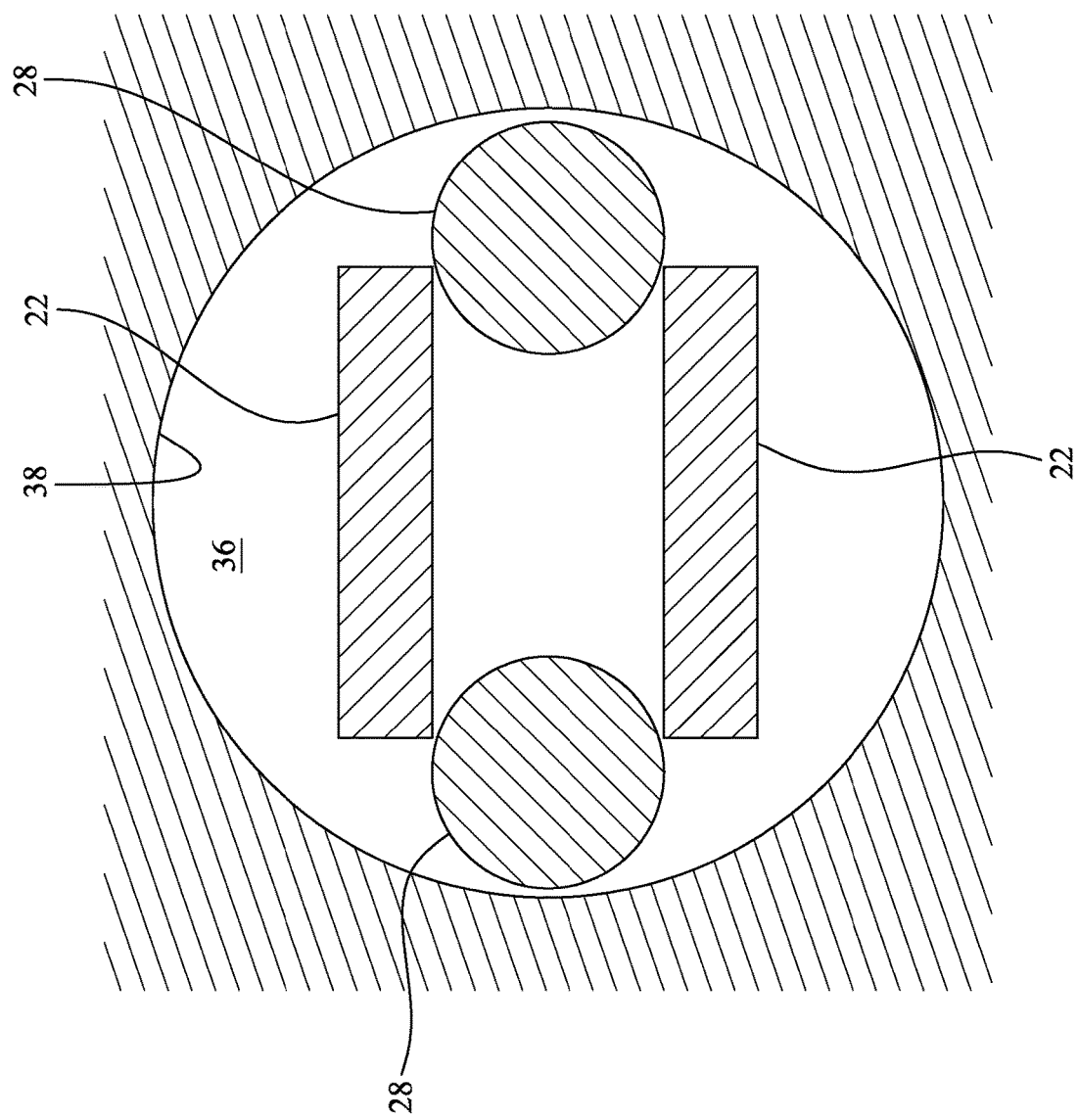
FIG. 3 is a close up, cross section, partial view of the bone, bone tunnel, and sutures at the dashed square marked F3 in FIG. 2.

As seen in FIGS. 2 and 3 the suture anchor 2 is ideal for situations where multiple sutures 22, 28 are used in a single bone tunnel 36 to connect, for example, two or more bones 38, a bone 38 and a ligament, and two or more bones 38 and a ligament. In the FIGS. 2 and 3, two bones 38 and a ligament are being connected (ligament not shown) with a suture tape first suture 22 and a suture strand second suture 28. The respective leading ends of each of the first and second sutures 22, 28 (extending downward and to the right in the page) would preferably be separately connected such the two strands of the first suture 22 are a single first suture strand and the two strands of the second suture 28 are a single second suture strand. See FIGS. 6 and 8B, for example.

The suture anchor 2 was developed to limit and potentially avoid interaction between multiple sutures 22, 28 converging in a single bone tunnel 36, in the situations in which two sutures 22, 28 are passed through a single bone tunnel. In the example shown, the first suture 22 is a suture tape characterized by a rectangular cross section while the second suture 28 is a suture strand illustrated with a circular cross section. These different shapes were chosen to better differentiate the sutures 22, 28, but it is conceived that suture anchor 2 will be able to host sutures with a variety of cross sections.

Figure 4:
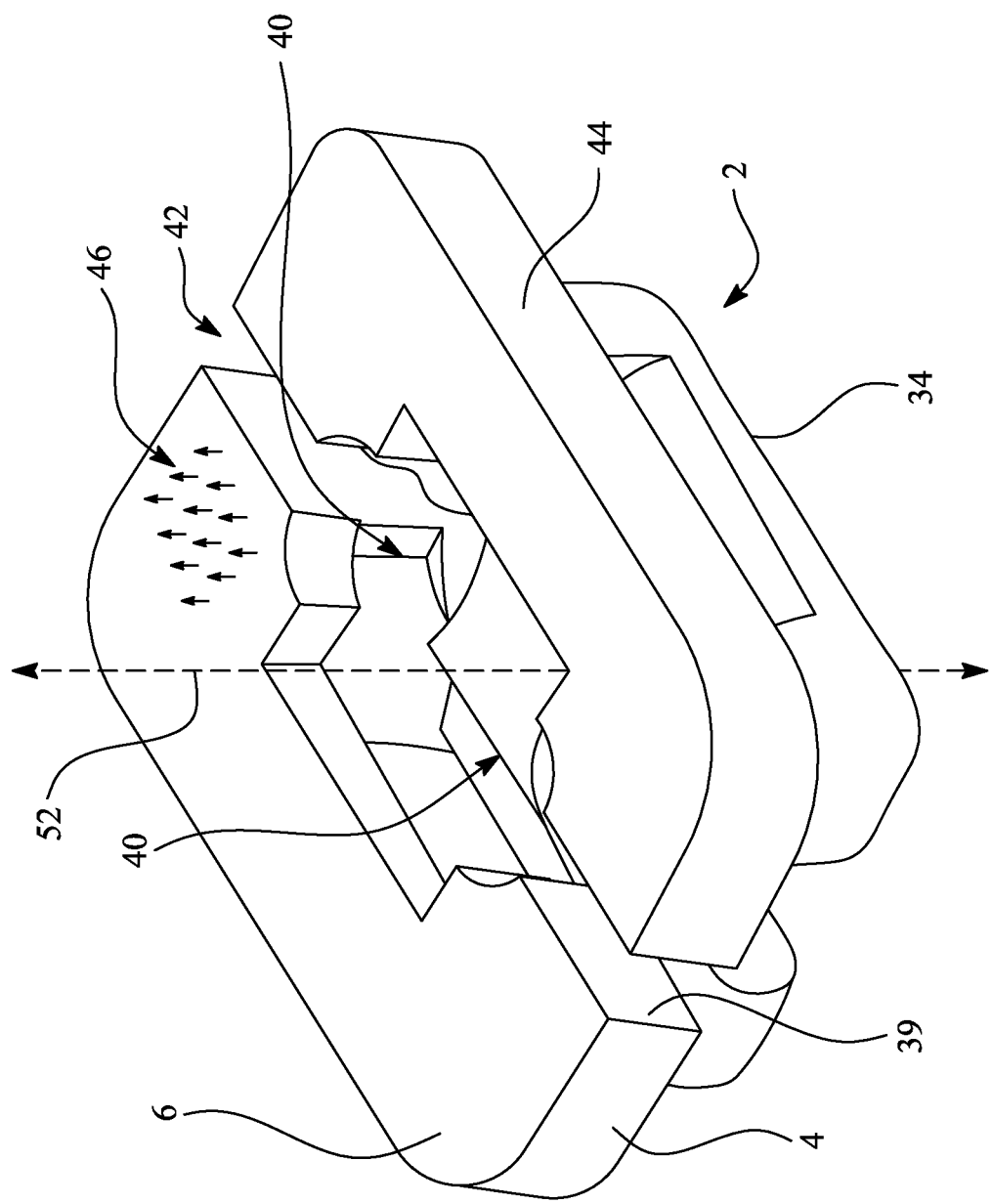
FIG. 4 is a bottom perspective view of an additional embodiment of the suture anchor disclosed herein.
Figure 11:
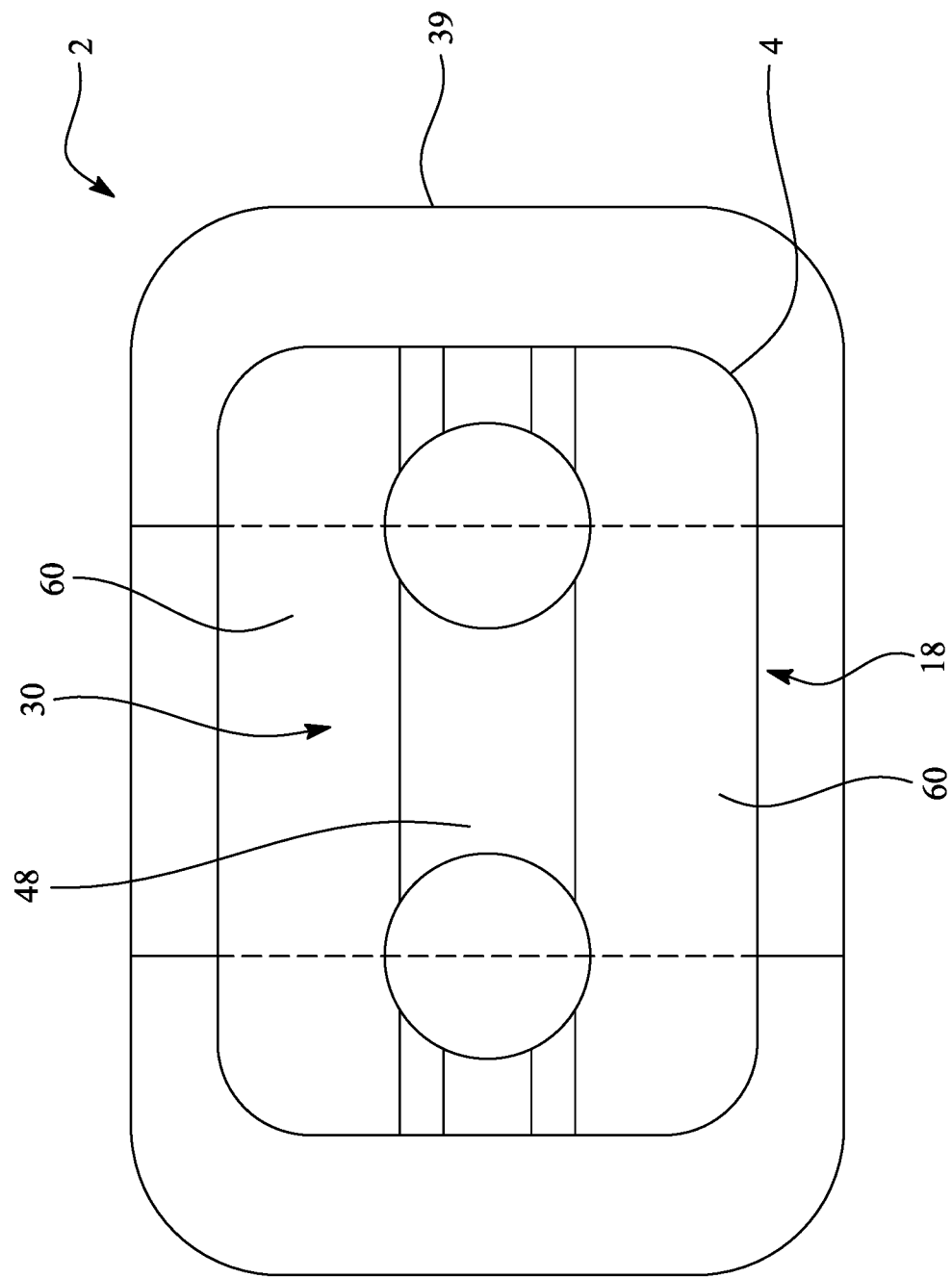
FIGS. 11 and 12 are overhead views of further embodiments of the suture anchor disclosed herein.

The base 6 is a bottom, bone 38 facing surface of a footing 39 portion of the body 4. The base 6 is preferably substantially planar. The base 6 defines one or more central openings 40, which function as the first, the second, the third, and the fourth base suture passages 8, 10, 12, 14 for the sutures 22, 28. While the four base suture passages 8, 10, 12, 14 are joined together in one central opening 40 in the embodiment shown, they could remain separately defined by the base 6, such that the base defines four separate openings. The central opening 40 can have a closed profile as shown in FIG. 11. Alternatively, as shown in FIG. 4, the central opening 40 can also have lateral openings 42 to a periphery 44 of the base 6 to more easily insert the sutures 22, 28 into the suture anchor 2. This allows the second suture 28 to be quickly engaged with the suture anchor 2, wrapping around the suture channel and passing through the lateral openings 42 to fit within the third and fourth 12, 14 base suture passages, all without having to thread or axially push the second suture 28 through the third and fourth base suture passages 12, 14. Though the lateral opening 42 is only shown for the third and fourth base suture passages 12, 14, alternatively or additionally, lateral openings 42 could be provided for the first and the second base suture passages 8, 10. The central opening 40 can be shaped with a simple geometric primitive such as a circle or shaped to resemble the cross sections of the sutures 22, 28 adopted, or, as shown in FIG. 4, as a Boolean union of rectangles and circles—or the union of two large rectangles (forming one large rectangle) matching the suture tape first suture 22 and two smaller circles matching the suture strand second suture 28.

Figure 13:
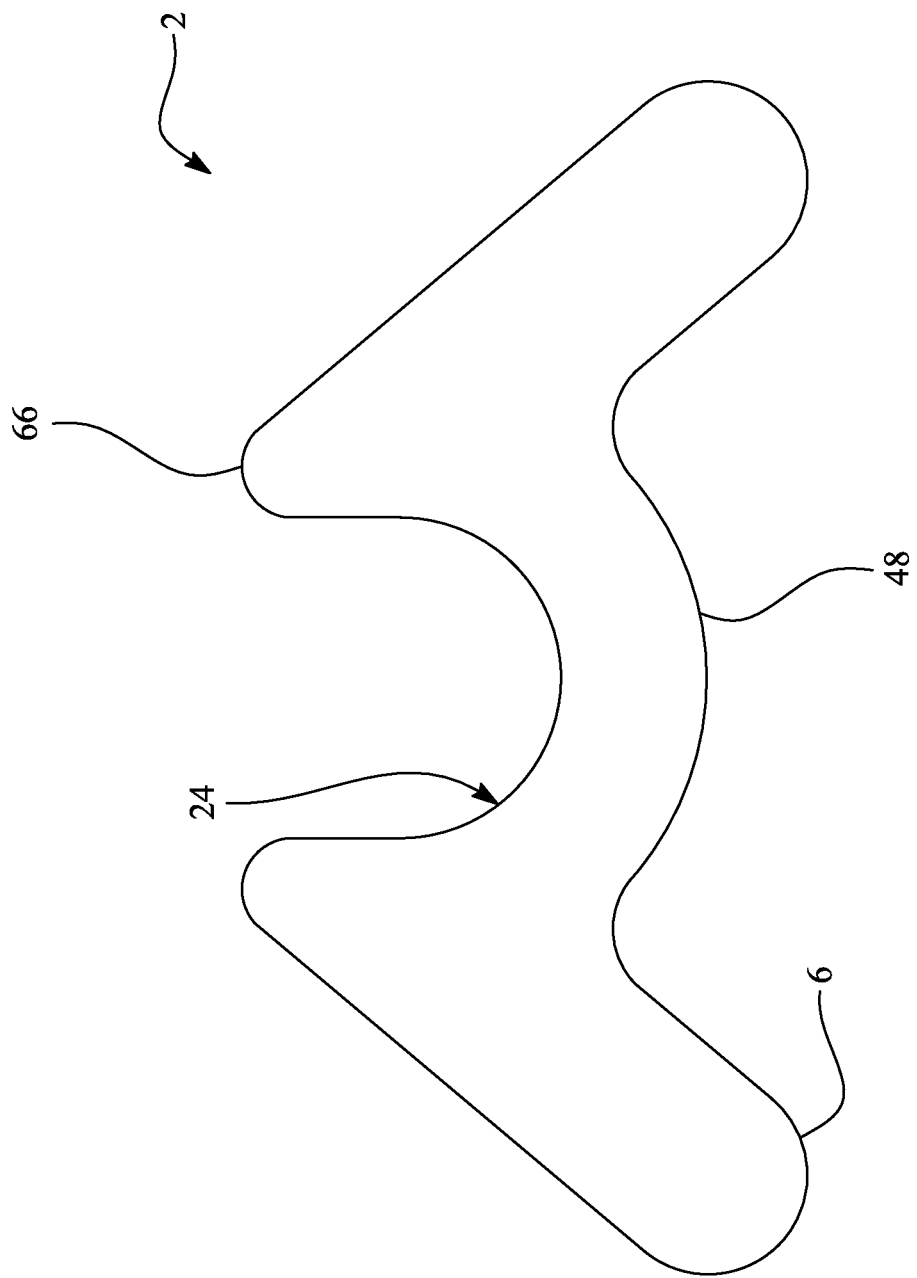
FIGS. 13-15 are respective front plan, overhead, and perspective views of the suture anchor of FIG. 1.
Figure 14:
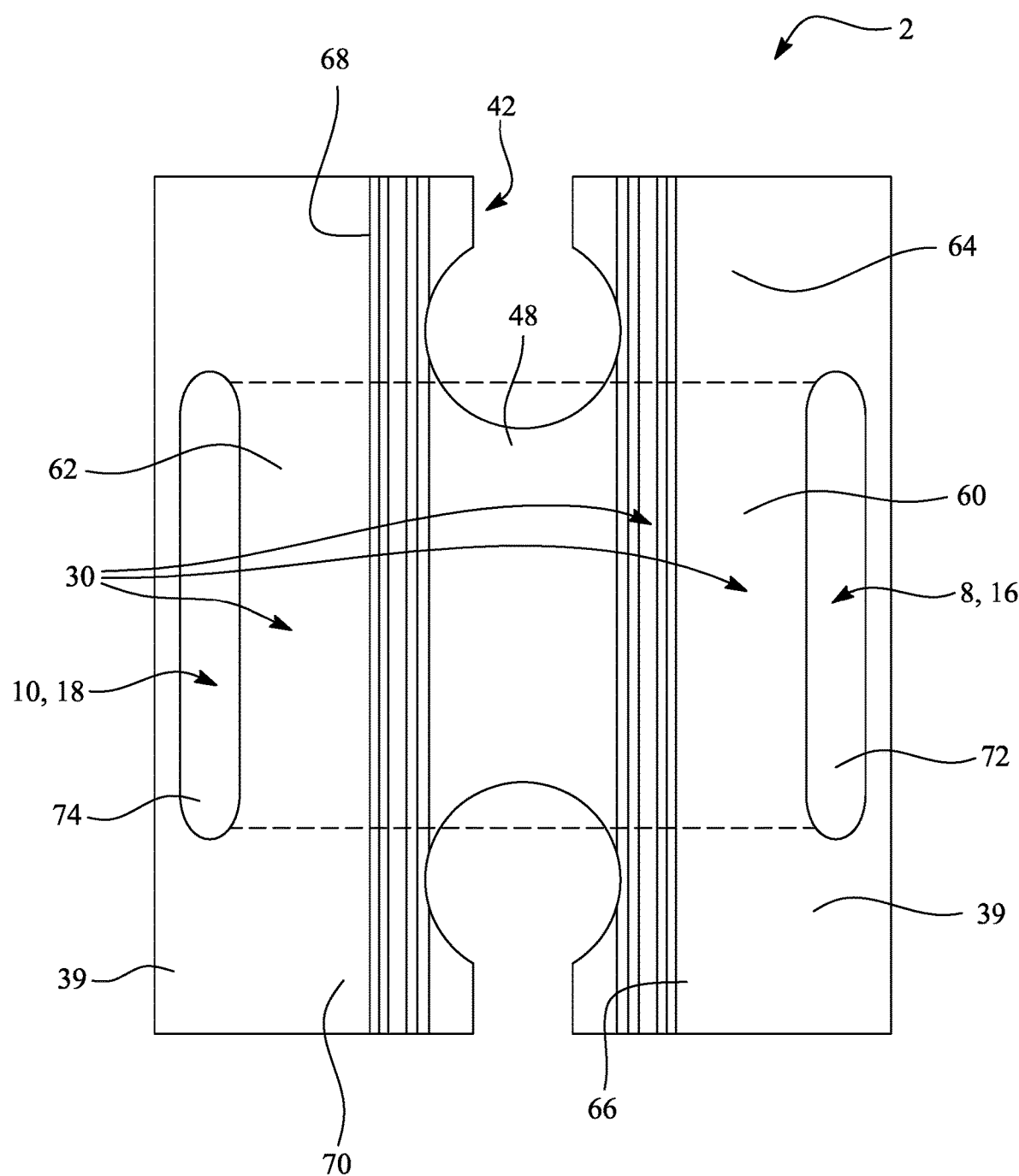
Figure 15:
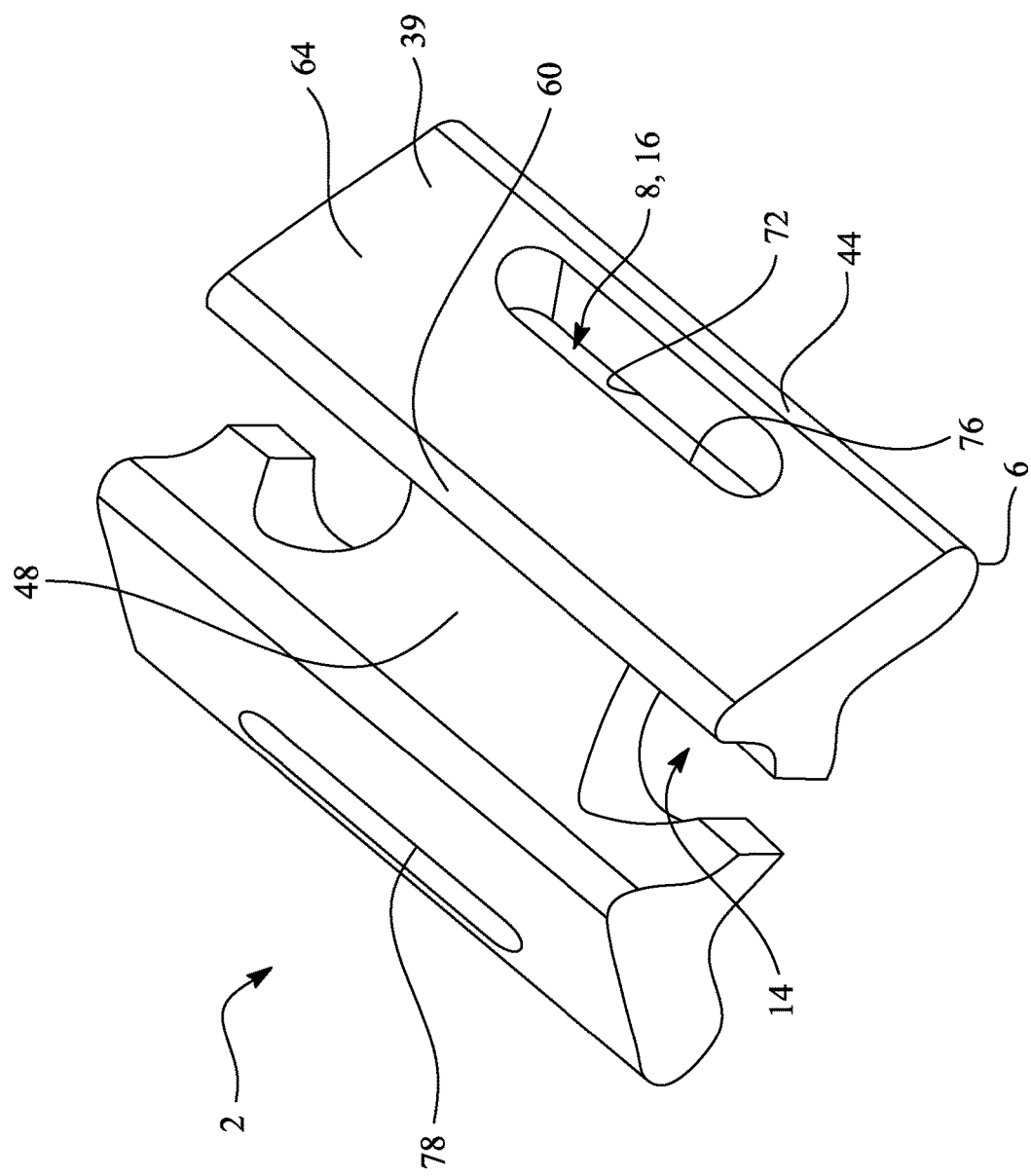
Figure 16A:
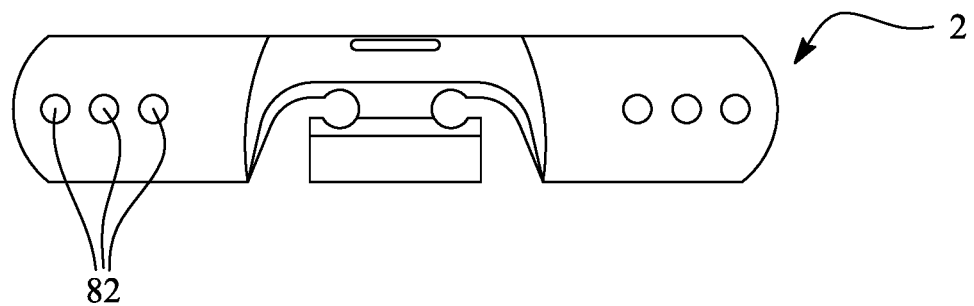
FIGS. 16A-16C are respective overhead, top perspective, and bottom perspective views of a further embodiment of the suture anchor disclosed herein.
Figure 16B:
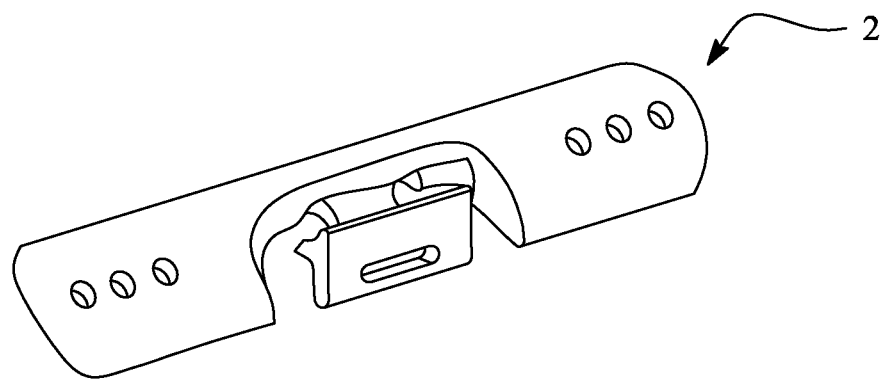
Figure 16C:
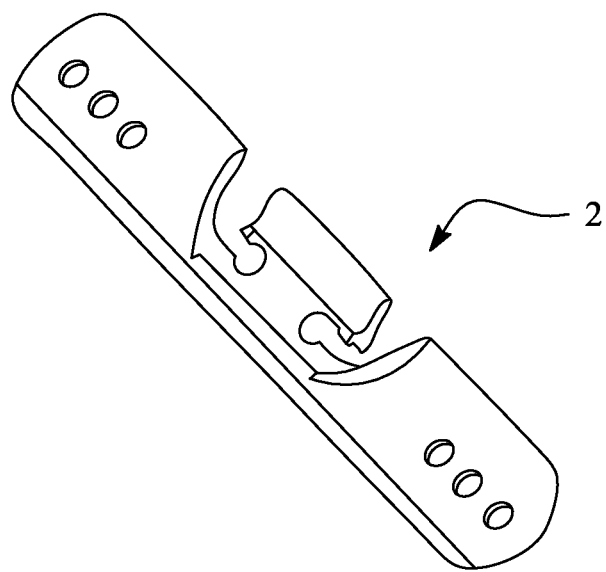
Figure 17A:
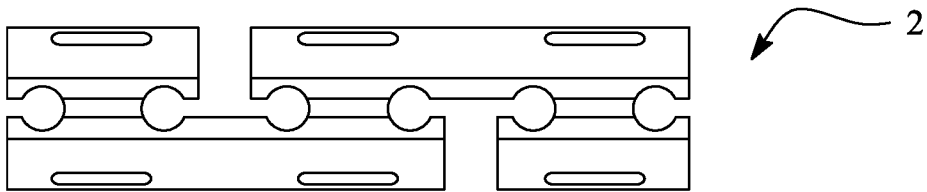
FIG. 17A-17C are respective overhead, top perspective, and bottom perspective views of a further embodiment of the suture anchor disclosed herein.
Figure 17B:
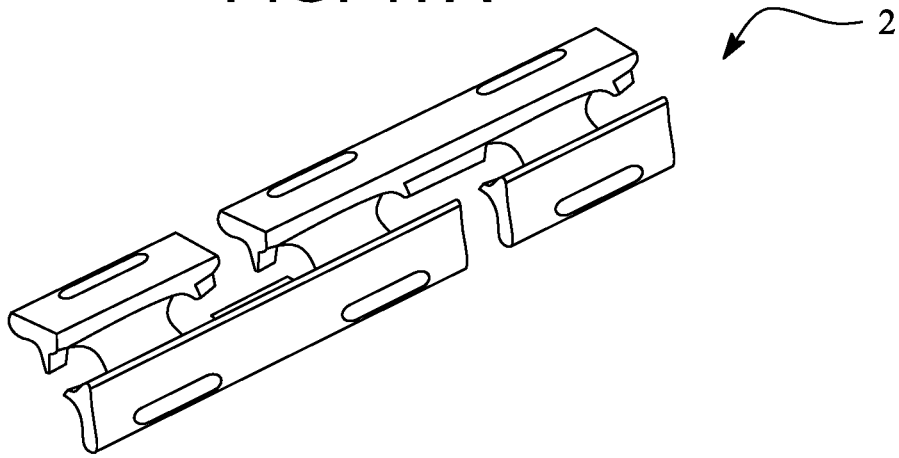
Figure 17C:
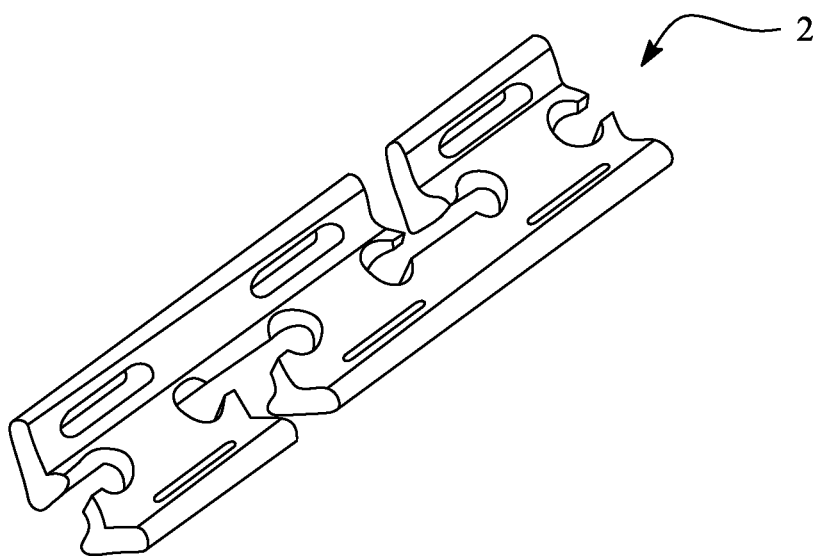
Figure 18A:
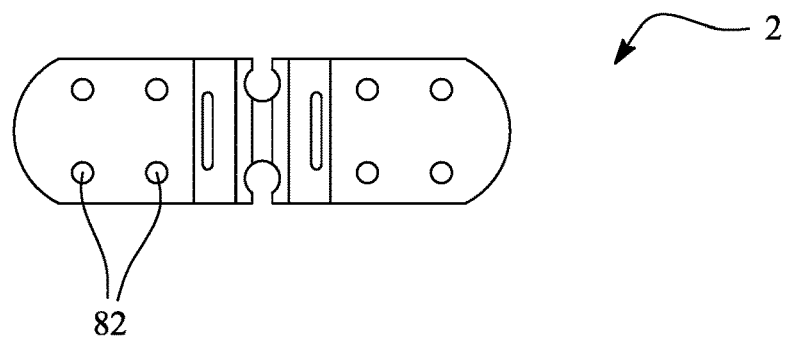
FIGS. 18A-18C are respective overhead, top perspective, and bottom perspective views of a further embodiment of the suture anchor disclosed herein.
Figure 18B:
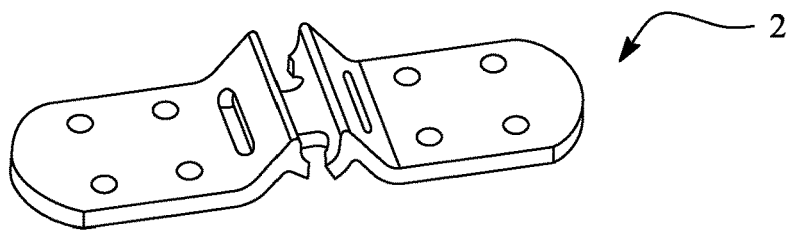
Figure 18C:
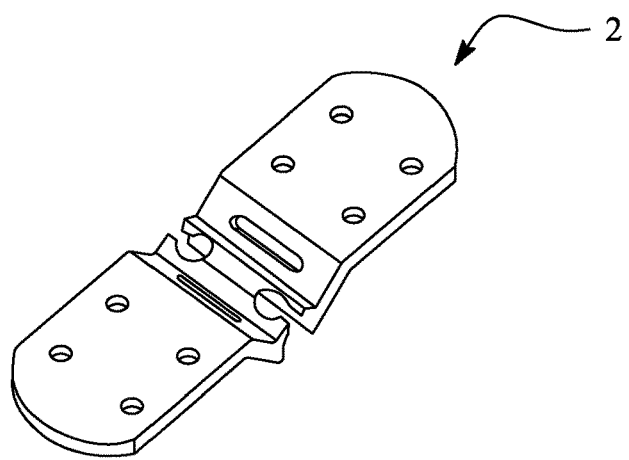

The base 6 of the suture anchor 2 defines a surface that can be planar, curved with a convex and/or concave down curvature in one or two directions, shaped to resemble the specific patient anatomy to which the base 6 will be abutting, kinked with two planar portions attached to each other at an angle, or may be a combination of these attributes, such as, for one example, in FIGS. 13-15, where two planar angled side portions are attached to a medial link 48, with a downwardly convex protrusion 50. The base 6 may be smooth and unitary of construction with the rest of the body 4, or the base may have surface features 46 that promote retention of the suture anchor in place with the bone. The surface features 46 may be of unitary construction as the rest of the body 4, or may be formed of a different material. Such surface features 46 may include a plurality of bumps and/or spikes, and/or a material/chemical covering to promote integration with bone 38. An example of spikes surface features 46 is shown in one portion of the base 6 in FIG. 4, but could be over all of the base 6 or none of the base 6 or in varying areas of the base 6.

Also shown in FIG. 4 is a central vertical axis 52, which intersects and is orthogonal to a first central lateral axis 54 and a second central lateral axis 56, with each axis intersecting and being orthogonal to the other two.

Figure 5A:
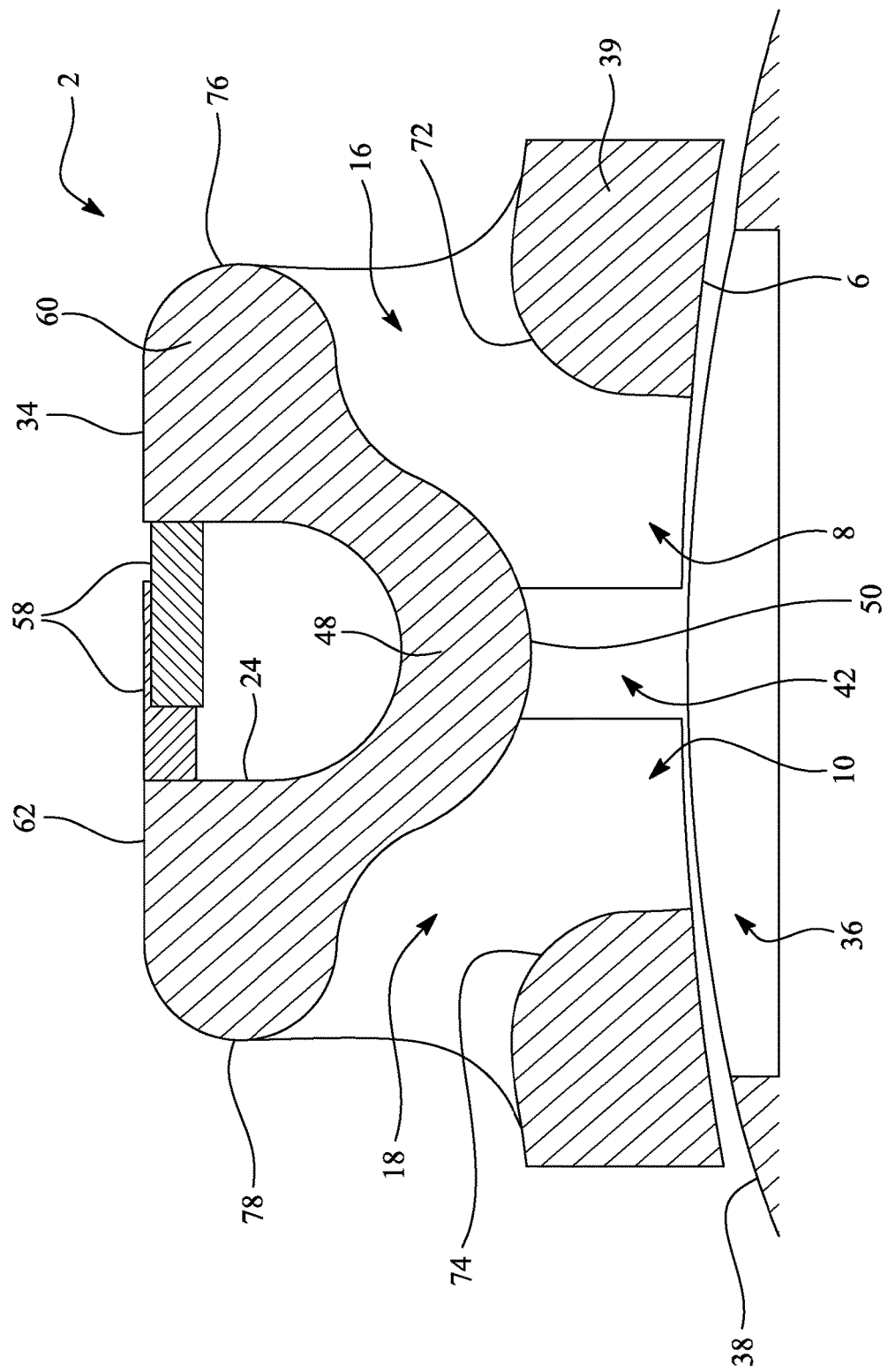
FIG. 5A is a cross sectional view of the suture anchor of FIG. 8A, along the sectional line FSA, mounted on a bone over a bone tunnel, but also with cantilevered side arms of the suture anchor of FIG. 12.

Turning to FIGS. 5A through 9, related embodiments of the suture anchor 2 are shown. In FIG. 5A, the drawing shows how the first primary suture passage 16 merges with the first base suture passage 8, and the second primary suture passage 18 merges with the second base suture passage 10. In FIGS. 5A, 8A, and 8B, for example, the upper portion of the body 4 is shown to include a first bridge 60 that is connected to the footing by first and second corner junctures 64, 66, and a second bridge 62 that is connected to the footing by third and fourth corner junctures 68, 70.

The bridges 60, 62 are spaced from the footing and define the first and second primary suture passages 16, 18 respectively. Looking at the cross sections, the first bridge 60 has a first elbow 76 that extends laterally outward parallel to the first central lateral axis 54 preferably approximately a width of the bone tunnel 36 the suture anchor 2 mounts on. The second bridge 62 has a second elbow 78 that extends laterally outward parallel to the first central lateral axis 54 and opposite to the direction of the first elbow 76.

The footing 39 portion of the first and second primary suture passages 16, 18 have a respective first and second lip 72, 74 that extend inwardly toward each other and toward the central vertical axis 52 parallel to the first central lateral axis 54. The respective lips 72, 74 preferably extend between ⅛ and ½, more preferably between ⅙ and ⅓ and most preferably about ¼ the lateral distance from a lateral extension of a respective elbow 76, 78 to a lateral midpoint of the suture anchor—which is preferably aligned with the low point of the convex protrusion and the second central lateral axis 56. This aids in putting greater lateral inward and downward force on the suture anchor 2 when in use. Also, this helps to space the first suture 22 from a wall of the bone 38 in the bone tunnel.

Figure 5B:
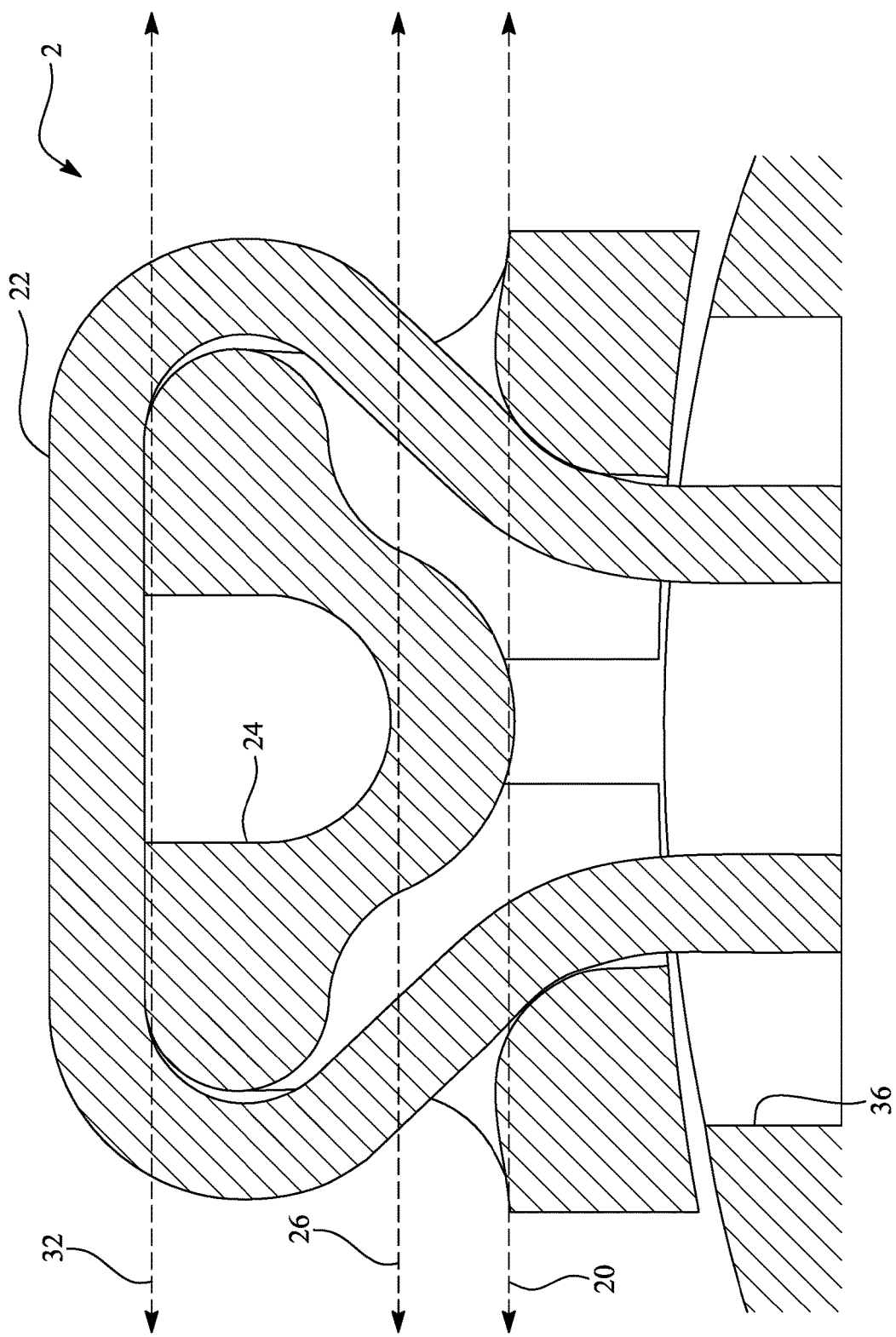
FIG. 5B is a cross sectional view of the suture anchor and suture tape of FIG. 6, along the sectional line FSB, mounted on a bone over a bone tunnel.
Figure 6:
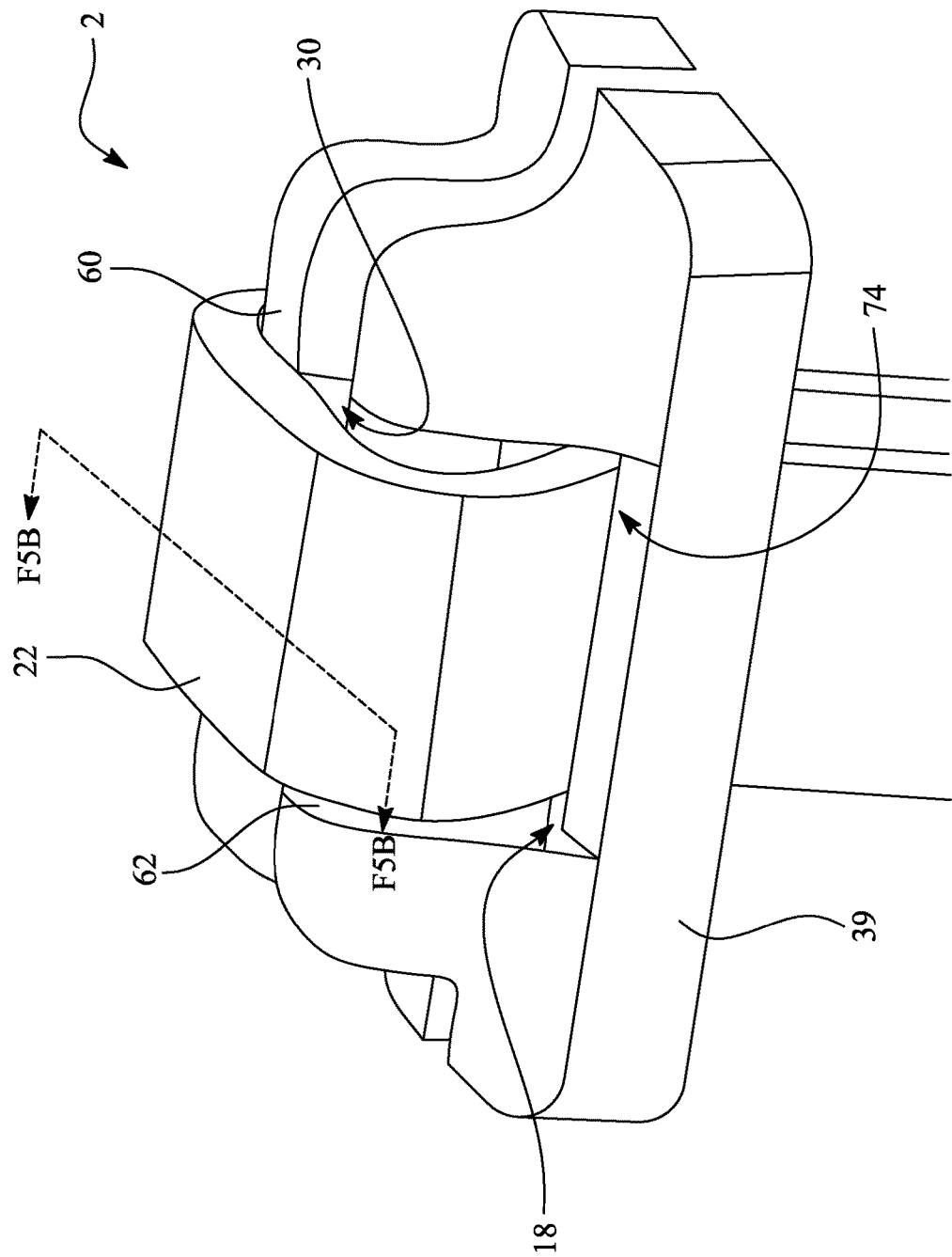
FIG. 6 is a top perspective view of the suture anchor of FIG. 4 with a suture tape inserted.
Figure 8A:
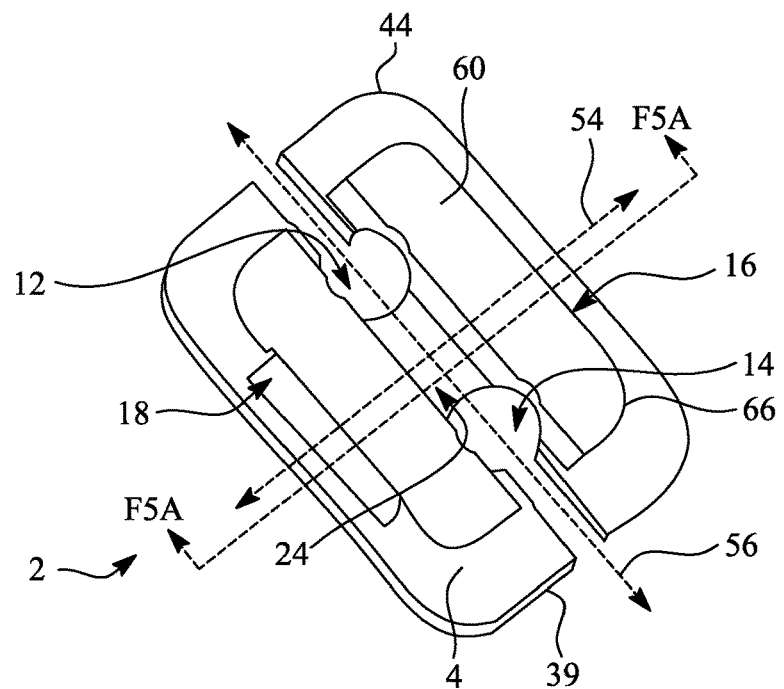
FIG. 8A is a top perspective view of the suture anchor of FIG. 4.
Figure 8B:
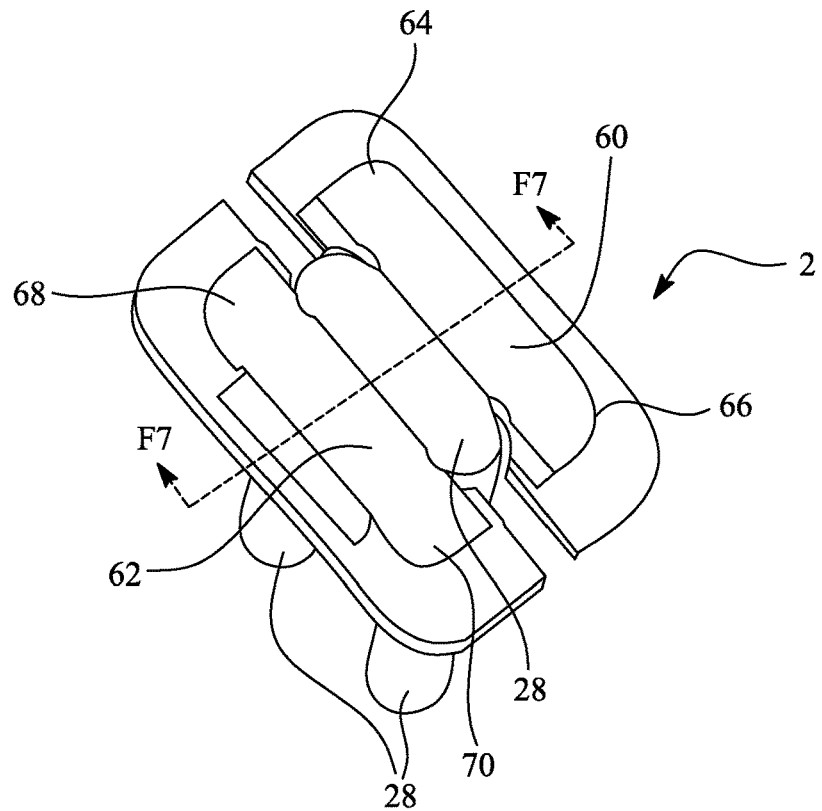
FIG. 8B is a top perspective view of the suture anchor of FIG. 8A with a suture strand inserted.

Turning to FIG. 5B, for example, the spacing between the primary, secondary, and tertiary 20, 26, 32 levels is shown. In the embodiment shown, the vertical spacing between the primary and secondary levels 20, 26 is about ½ the vertical distance between the secondary and tertiary levels 26, 32. In other embodiments the ratio could be ¼, ⅓, ⅔, and ¾. The spacing allows for proper tensioning, compactness, while preventing the first and second sutures 22, 28 from pulling on one another.

In operation, the sutures 22, 28 enter the suture anchor 2 from this central opening 40 and turn around surfaces disposed on the separated secondary and tertiary levels 26, 32, with the first suture 22 wrapping around the first and second bridges 60, 62, across the top 34 of the suture anchor 2 along the suture course 30 and on the tertiary level 32 and in line with the first central lateral axis 54. The second suture 28 wraps around the medial link 48 and in the suture channel on the secondary level 26 and in line with the second central lateral axis 26. The separation between these two levels 26, 32 is key to limitation of interaction between the sutures 22, 28 according to some embodiments. It is noted that the sutures are preferably aligned orthogonally to one another, but because of the inventive vertical separation, they two sutures 22, 28 do not interfere with each other.

Turning to FIGS. 5A and 5B again the cross-section shows the organization of the bearing surfaces in the distinguished levels 20, 26, 32. As shown in FIG. 5B, the first suture 22 lays on the elbows 76, 78 and is urged inward by the lips 72, 74 on the footing 39 by the central opening 40 at the base 6 where the first suture 22 enters the bone tunnel 36 in the bone 38. The forces exercised by the lips 72, 74 at the footing 39 also reduces or avoids the radial expansion of the bone tunnel 36 in the bone 38.

Figure 9:
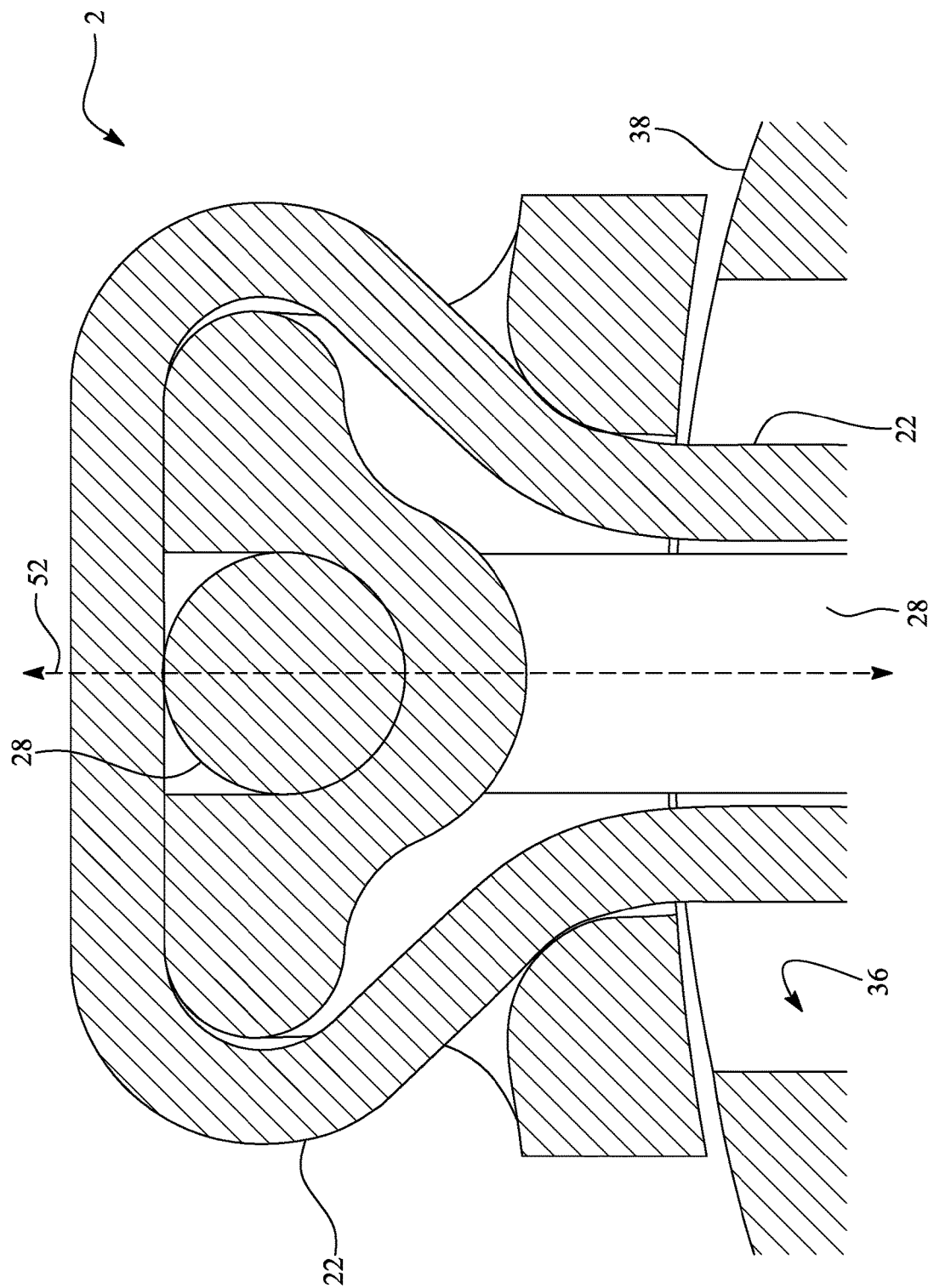
FIG. 9 is a cross sectional view of the suture anchor with suture strand and suture tap of FIG. 10, along the sectional line F9, mounted on a bone over a bone tunnel.
Figure 10:
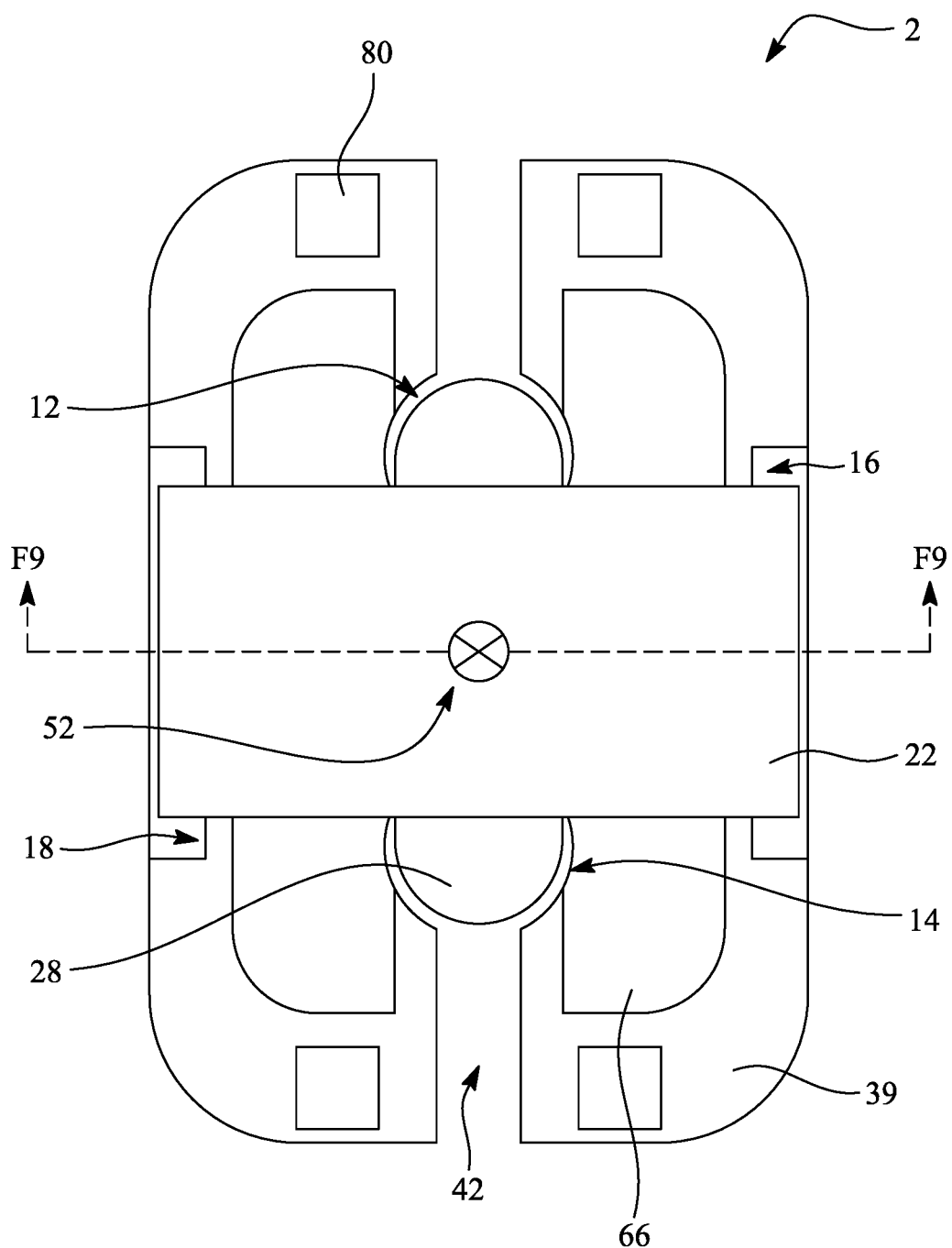
FIG. 10 is an overhead view of the suture anchor of FIG. 8A, with perimeter notches, and with both a suture strand and a suture tape inserted.

In the cross-section of FIG. 9 shows both sutures 22, 28 simultaneously visible, and the limited interference between the two sutures 22, 28 is apparent. To aid in easy insertion the suture anchor 2 can also have perimeter notches 80 disposed thereon to facilitate the attachment of tools needed for the insertion. The perimeter notches 80 can be positioned anywhere on the suture anchor 2, and are here shown on this location on the footing 39 purely as example.

Figure 12:
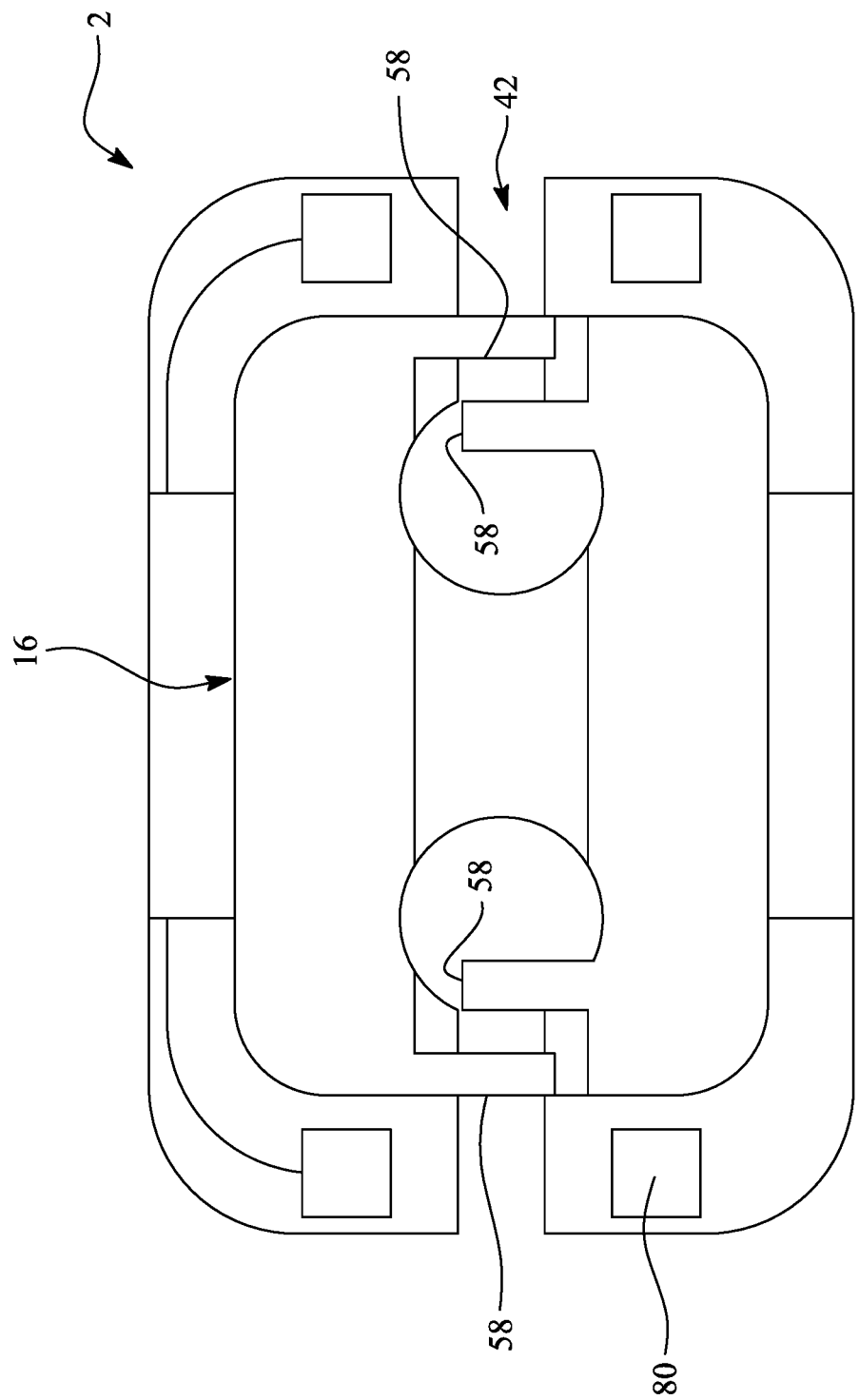

In two preferred embodiments, the base periphery 44 is not broken and lateral opening is not present, as shown in FIG. 11. Or, additionally/alternatively, as shown in FIGS. 5A and 12, the suture anchor 2 may be provided with cantilevered side arms 58 placed in the suture channel 24 hosting the second suture 28, to limit the bending of the suture anchor 2 when in use.

In an additional embodiment shown in FIGS. 1, 13-15, the four corner junctures 64, 66, 68, 70 of the suture anchor 2 are not perpendicular to the base 6 but are inclined and the base 6 of the suture anchor 2 is effectively fully contained in the inner facing portion of the corner junctures 64, 66, 68, 70 and the footing 39.

Turning to FIGS. 16A-18C, further embodiments of the suture anchor 2 are shown. In two embodiments that integrate curved or planar bone plates with fastener holes 82 along the second central lateral axis 56 in FIGS. 16A-16C, or along the first central lateral axis 54 in FIGS. 18A-18C, for example In a further embodiment, a plurality of suture anchor 2 units are formed together, here with lateral openings at alternating lateral sides of the suture anchor. In this embodiment, there are four lateral openings, one disposed in each lateral side. This allows the increased threading speed of lateral openings, but distributes the attendant structural weakness, apportioning a bit on each side. Though three subunits are shown in this embodiment, and there are advantages to such a number, the number could be two, or four, or five or more, depending on the need of the patient.

The suture anchors disclosed herein may be made of stainless steel, titanium, or other sufficiently strong and non-bioactive material. The suture anchor of FIG. 1 measures 10×6×2 mm but considered that same design can be used for different sutures and joints, a variability in dimensions and proportions are be conceived.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," "having" and variations thereof herein is meant to encompass the items listed thereafter and equivalents thereof as well as additional items while only the terms "consisting of" and "consisting only of" are to be construed in the limitative sense.

We claim:

1. A surgical suture button system comprising:
   a first and a second bridge portion comprising a respective first and a second top surface, the first and the second top surfaces sharing a first central axis, the first central axis defining a first suture course; and
   a medial link member integral to the first and the second bridge portions, wherein the medial link member comprises a medial suture channel disposed below the first and the second top surfaces of the first and the second bridge portions; and
   wherein the medial suture channel is disposed below and is substantially perpendicular to the first suture course.

2. The suture button of claim 1, further comprising:
   a first suture and a second suture;
   a footing with a base defining a first, a second, a third, and a fourth base suture passage, the base designed to contact bone or other tissue being sutured and to transmit force from the button to the bone or other tissue, the first base suture passage being an entrance to the suture button for the first suture, the second base suture passage being an exit from the suture button for the first suture, the third base suture passage being entrance to the suture button for the second suture, and the fourth base suture passage being an exit from the suture button for the second suture;
   a first and a second primary suture passage for the first suture to pass through, the first and the second primary suture passage being aligned with a primary level and being respectively the first and second base suture passages, the primary level defining a plane substantially parallel with the base;
   wherein the medial suture channel is aligned with a secondary level and connected to the third and fourth base suture passages, the secondary level defining a plane substantially parallel with the base;
   wherein the first suture course is aligned with a tertiary level defined by the first and the second top surfaces, the tertiary level being spaced further from the base than both the primary and secondary level, the suture course being connect to the first and the second primary suture passage, and the tertiary level defining a plane substantially parallel with the base; and
   wherein a central vertical axis intersects the suture channel in the secondary level and the suture course in the tertiary level.

3. The suture button of claim 2, wherein the four base suture passages are joined together in one central opening.

4. The suture button of claim 3, wherein the central opening has a closed profile defined by a periphery of the base.

5. The suture button of claim 3, wherein the central opening has an open profile defined by a periphery of the base, the base defining lateral openings between the central opening and a base periphery.

6. The suture button of claim 2 wherein a vertical spacing measured along the central vertical axis between the primary and the secondary levels is between ¼ and ¾ a vertical spacing between the secondary and tertiary levels.

7. The suture button of claim 2 wherein the first and the second bridge portion are spaced from the base, the footing has a respective first and a second lip that extend inwardly toward each other and toward the central vertical axis, wherein a lower surface of the first bridge portion defines an upper surface of the first primary suture passage, an upper surface of the first lip defines a lower surface of the first primary suture passage, a lower surface of the second bridge portion defines an upper surface of the second primary suture passage, an upper surface of the second lip defines a lower surface of the second primary suture passage.

8. The suture button of claim 7, wherein an upper surface of the first and the second bridge portions define a lower surface of the suture course.

9. The suture button of claim 8, wherein an upper surface of a medial channel defines a lower surface of the suture channel.

10. The suture button of claim 9, wherein the upper surface of the medial channel defining the lower surface of the suture channel is lower than the upper surface of the first and the second bridge defining the lower surface of the suture course.

11. The suture button of claim 1 further comprising surface features on a base that promote retention of the suture button in place with a bone or a piece of tissue.

12. The suture button of claim 1, further comprising one or more fastener holes defined on either lateral side of the suture button.

13. The surgical suture button system of claim 1, further comprising a first suture and a second suture, wherein:
   the first suture slidably engages with the first suture course;
   the second suture slidably engages with the medial suture channel; and
   the first suture course and the medial suture channel are configured to prevent contact between the first suture and the second suture.

14. A surgical suture button system for anchoring multiple sutures, comprising:
   (a) a first suture and a second suture;
   (b) a right body section having a top surface and a base, the right body section comprising: (i) a first footing portion positioned adjacent to the base of the right body section; (ii) a first bridge portion positioned adjacent to the top surface of the right body section; and (iii) a first intermediary juncture portion connecting the first bridge portion to the first footing portion, wherein the first intermediary juncture portion comprises a first primary suture passage adapted to receive a first portion of the first suture;
   (c) a left body section having a top surface and a base, the left body section comprising: (i) a second footing portion positioned adjacent to the base of the left body section; (ii) a second bridge portion positioned adjacent to the top surface of the left body section; and (iii) a second intermediary juncture portion connecting the second bridge portion to the second footing portion, wherein the second intermediary juncture portion comprises a second primary suture passage adapted to receive a second portion of the first suture; and
   (d) a medial link connecting the first bridge portion of the right body section to the second bridge portion of the left body section, the medial link defining a medial channel positioned below the top surfaces of the right and left body sections, wherein the medial channel comprises: (i) a first medial suture passage adapted to receive a first portion of the second suture, (ii) a second medial suture passage adapted to receive a second portion of the second suture, and (iii) a central imperforate bridge intermediate the first medial suture passage and the second medial suture passage configured to be in contact with the second suture; and wherein the first and the second bridge portion provide a suture course for the first suture, the suture course substantially perpendicular to and positioned above the medial channel.

15. The surgical suture button of claim 14, wherein the left body section is oblique relative to the right body section, with the first and second bridge portions being non-coplanar and positioned closer together than the first and second footing portions.

16. The surgical suture button of claim 15, wherein the first bridge portion comprises a first elbow defining an upper wall of the first primary suture passage, and wherein the first footing portion comprises a first lip defining a lower wall of the first primary suture passage.

17. The surgical suture button of claim 16, wherein the second bridge portion comprises a second elbow defining an upper wall of the second primary suture passage, and wherein the second footing portion comprises a second lip defining a lower wall of the first primary suture passage.

18. The surgical suture button of claim 17, wherein the first and second medial lateral openings are positioned at opposing ends of the medial channel.

19. The surgical suture button of claim 18, wherein the first primary suture passage comprises a first base opening adjacent to the first footing portion, wherein the second primary suture passage comprises a second base opening adjacent to the second footing portion, and wherein the first and second medial suture passages each comprise medial base openings positioned between the first and second base openings.

20. A surgical suture button for anchoring multiple sutures, comprising:
(a) a right body section comprising: (i) a top surface; (ii) a base surface; (iii) a first footing portion positioned adjacent to the base surface of the right body section; (iv) a first bridge portion positioned adjacent to the top surface of the right body section; and (v) a first intermediary juncture portion connecting the first bridge portion to the first footing portion, wherein the first intermediary juncture portion comprises a first primary suture passage adapted to receive a first portion of the first suture;
(b) a left body section comprising: (i) a top surface; (ii) a base surface; (iii) a second footing portion positioned adjacent to the base surface of the left body section; (iv) a second bridge portion positioned adjacent to the top surface of the left body section; and (v) a second intermediary juncture portion connecting the second bridge portion to the second footing portion, wherein the second intermediary juncture portion comprises a second primary suture passage adapted to receive a second portion of the first suture;
(c) a medial link connecting the first bridge portion of the right body section to the second bridge portion of the left body section, the medial link defining a medial channel positioned below the top surfaces of the right and left body sections, wherein the medial channel comprises: (i) a first medial suture passage adapted to receive a first portion of a second suture; (ii) a second medial suture passage adapted to receive a second portion of the second suture, and (iii) a central imperforate bridge positioned between the first medial suture passage and the second medial suture passage and configured to be in contact with the second suture; and wherein the first and the second bridge portions provide a suture course positioned above and substantially perpendicular to the medial channel.

\* \* \* \* \*